United States Patent
Dang et al.

(10) Patent No.: US 11,760,973 B2
(45) Date of Patent: *Sep. 19, 2023

(54) METHOD FOR IMPROVING EXPANSION OF T CELLS FROM PATIENTS

(71) Applicant: The Trustees of Columbia University in the City of New York, New York, NY (US)

(72) Inventors: Alex Dang, New York, NY (US); Lance C. Kam, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 993 days.

This patent is subject to a terminal disclaimer.

(21) Appl. No.: 16/098,851

(22) PCT Filed: May 3, 2017

(86) PCT No.: PCT/US2017/030923
§ 371 (c)(1),
(2) Date: Nov. 3, 2018

(87) PCT Pub. No.: WO2017/192776
PCT Pub. Date: Nov. 9, 2017

(65) Prior Publication Data
US 2019/0127686 A1 May 2, 2019

Related U.S. Application Data (60) Provisional application No. 62/405,064, filed on Oct. 6, 2016, provisional application No. 62/331,381, filed on May 3, 2016.

(51) Int. Cl.
| | | |
|---|---|---|
| *C12N 5/00* | (2006.01) | |
| *A61K 35/17* | (2015.01) | |
| *D06M 15/507* | (2006.01) | |
| *D04B 21/12* | (2006.01) | |

(52) U.S. Cl.
CPC ............ *C12N 5/0068* (2013.01); *A61K 35/17* (2013.01); *D04B 21/12* (2013.01); *D06M 15/507* (2013.01); *C12N 2533/30* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 7,998,736 | B2 | 8/2011 | Morgan et al. |
| 9,005,607 | B2 | 4/2015 | Kumar et al. |
| 2002/0058019 | A1* | 5/2002 | Berenson ............ A61L 27/3895 424/93.7 |
| 2003/0194395 | A1 | 10/2003 | Gruenberg et al. |
| 2008/0153163 | A1* | 6/2008 | Mao ..................... C12N 5/0641 435/377 |
| 2011/0196328 | A1 | 8/2011 | Bellini et al. |
| 2013/0214457 | A1 | 8/2013 | David et al. |
| 2015/0030619 | A1* | 1/2015 | Milone ............... C12N 5/0636 435/375 |
| 2017/0029767 | A1 | 2/2017 | Kam et al. |

FOREIGN PATENT DOCUMENTS

| | | | |
|---|---|---|---|
| WO | 2015157664 | A2 | 10/2015 |
| WO | WO-2015157664 | A2 * | 10/2015 ............. A61K 35/17 |

OTHER PUBLICATIONS

Bashour et al., "CD28 and CD3 have complementary roles in T-Cell traction forces", Proc. Natl Acad Sci U S A, vol. 111, Issue 6, pp. 2241-2246, Feb. 11, 2014.
Kam, "Advanced Rigidity-Based Material for Enhanced Immunotherapy", NIH Project# 5R01AI110593-02, Awardee Organization: Columbia University New York Morningside.
Kam, "Controllable Rigidity Surfaces For T Cell Mechanobiology", NIH Project# IR21AI119953-01A1, Awardee Organization: Columbia University New York Morningside.
Kam, "Sample Sparing Chambers For Imaging Of T Cell Response And Function", NIH Project #1U24AI118669-01, Awardee Organization: Columbia University New York Morningside.
Tabdanov et al., "Micropatterning of TCR and LFA-1 ligands reveals compleementary effects on cytoskeleton mechanics in T cells", Integrative Biology, vol. 7, Issue 10, pp. 1272-1284, Oct. 2015.
Bashour et al., "Cross Talk between CD3 and CD28 is Spatially Modulated by Protein Lateral Mobility," Molecular and Cellular Biology, vol. 34, No. 6, pp. 955-964, Mar. 2014.
Basu et al., "Cytotoxic T cells use mechanical force to potentiate target cell killing," Cell, vol. 165, No. 1, pp. 100-110, Mar. 2016.
Desantis et al., "Cancer Treatment and SurvivorshipStatistics, 2014," CA: A Cancer Journal of Clinicians, vol. 64, No. 4, pp. 252-271, 2014.
International Search Report and Written Opinion for International Application No. PCT/US2017/030923 dated Aug. 2, 2017.
June, "Principles of adoptive T cell cancer therapy," The Journal of Clinical Investigation, vol. 117, No. 5, pp. 1204-1212, May 2007.
Lee et al., "A microfluidic platform reveals differential response to regulatory T cells to micropatterned constimulation arrays," Integrative Biology, vol. 7, Issue 11, pp. 1442-1453, Nov. 2015.

(Continued)

Primary Examiner — Nghi V Nguyen
(74) Attorney, Agent, or Firm — Potomac Law Group, PLLC (57) ABSTRACT

In an aspect, compositions, methods, and devices described herein provide a safer platform for the ex vivo expansion of cells for immunotherapeutic purposes that eradicates the possibility of having activating substrate transferred into the patient while maintaining and improving upon the level of cell activation and proliferation.

5 Claims, 7 Drawing Sheets

(56) References Cited

OTHER PUBLICATIONS

O'Connor et al., "Substrate Rigidity Regulates Human T Cell Activation and Proliferation," The Journal of Immunology, vol. 189, pp. 1330-1339, Jun. 2012.
Dang et al., "Enhanced Activation and Expansion of T Cells Using Mechanically Soft Elastomer Fibers," Advanced Biosystems, p. 1700167, 2018.

* cited by examiner

METHOD FOR IMPROVING EXPANSION OF T CELLS FROM PATIENTS

CROSS REFERENCE TO RELATED APPLICATIONS

This Application is a U.S. national stage filing under 35 U.S.C. § 371 of International Application No. PCT/US2017/030923, filed May 3, 2017, which claims the benefit of U.S. Provisional Application No. 62/331,381, filed May 3, 2016, and U.S. Provisional Application No. 62/405,064, filed Oct. 6, 2016, the content of each of these applications are herein incorporated herein by reference in their entirety.

STATEMENT OF GOVERNMENT SUPPORT

This invention was made with government support under R01AI110593 awarded by National Institutes of Health. The government has certain rights in the invention.

BACKGROUND

Adoptive immunotherapy holds great potential as a therapeutic modality for the treatment of a variety of diseases including cancer and chronic viral infections. Central to these therapeutic approaches are controllable platforms for ex vivo activation of T cells. Several cell-based and artificial substrate systems have been described (June 2007, J Clin Invest. 117(5): 1204-12).

Agonist antibodies to CD3 and CD28 immobilized on rigid materials, for example, polystyrene plastic and glass, have been utilized for the activation and expansion of T cells. However, T cells are unlikely to encounter a stimulatory surface with the stiffness of plastic in vivo, and the stiffness of the solid supports used for ex vivo culture of T cells may have important influences on their activation, proliferation, and differentiation that could impact their use in adoptive immunotherapy.

Current immunotherapy technologies reprogram T cells ex vivo to target leukemia. During this process, cells are transfected and expanded. One such method for facilitating T cell expansion involves Dynabeads™, for example, 4.5-um diameter polystyrene beads mixed with cells for high surface area-to-volume ratio. T cell signaling, proliferation, and expansion has been linked to the rigidity of the surface on which they are cultured—finding optimal expansion on "softer" surfaces (Young's Modulus or elastic modulus, "E," of bulk materials less than 100 kPa as compared to a Young's Modulus, E, of greater than 2 MPa).

However, there is a need to develop further expansion platforms that allow for the fine-tuning of surface and/or matrix rigidity while maintaining a high area-to-volume ratio, which can be important to cell culture and practicality of clinical use. To this end, the electrospun mesh described herein offers an improved area-to-volume ratio and has many parameters that can be altered to tune rigidity and additional properties of interest, for example, polymer composition, fiber diameter, and mesh porosity.

SUMMARY

In an aspect, compositions, methods, and devices described herein provide a safer platform for the ex vivo expansion of cells for immunotherapeutic purposes that eradicates the possibility of having activating substrate transferred into the patient while maintaining and improving upon the level of cell activation and proliferation.

Objects and advantages of embodiments of the disclosed subject matter will become apparent from the following description when considered in conjunction with the accompanying drawings.

Figure 1:
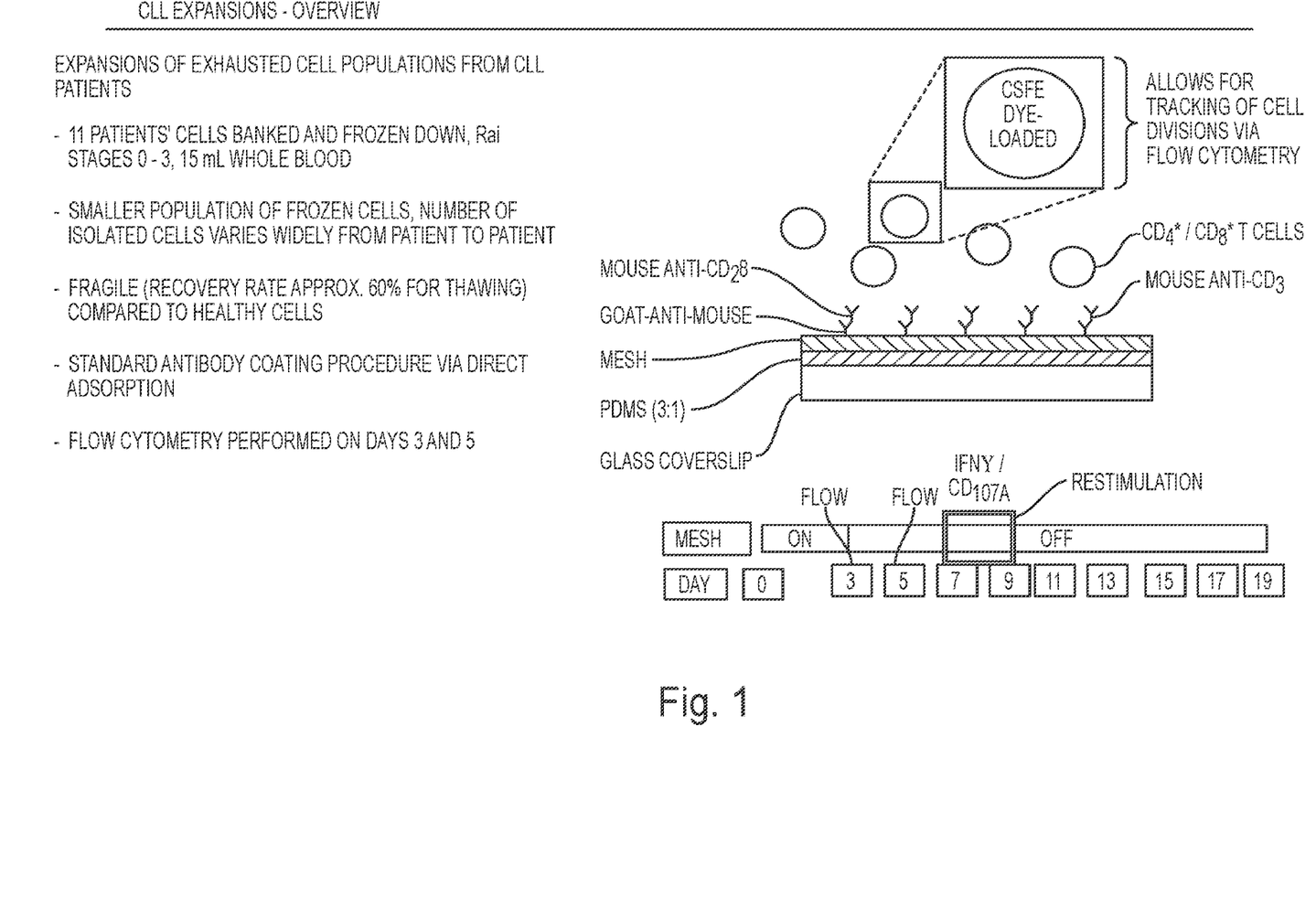
FIG. 1 shows an overview of the expansion process according to embodiments of the disclosed subject matter.
Figure 2:
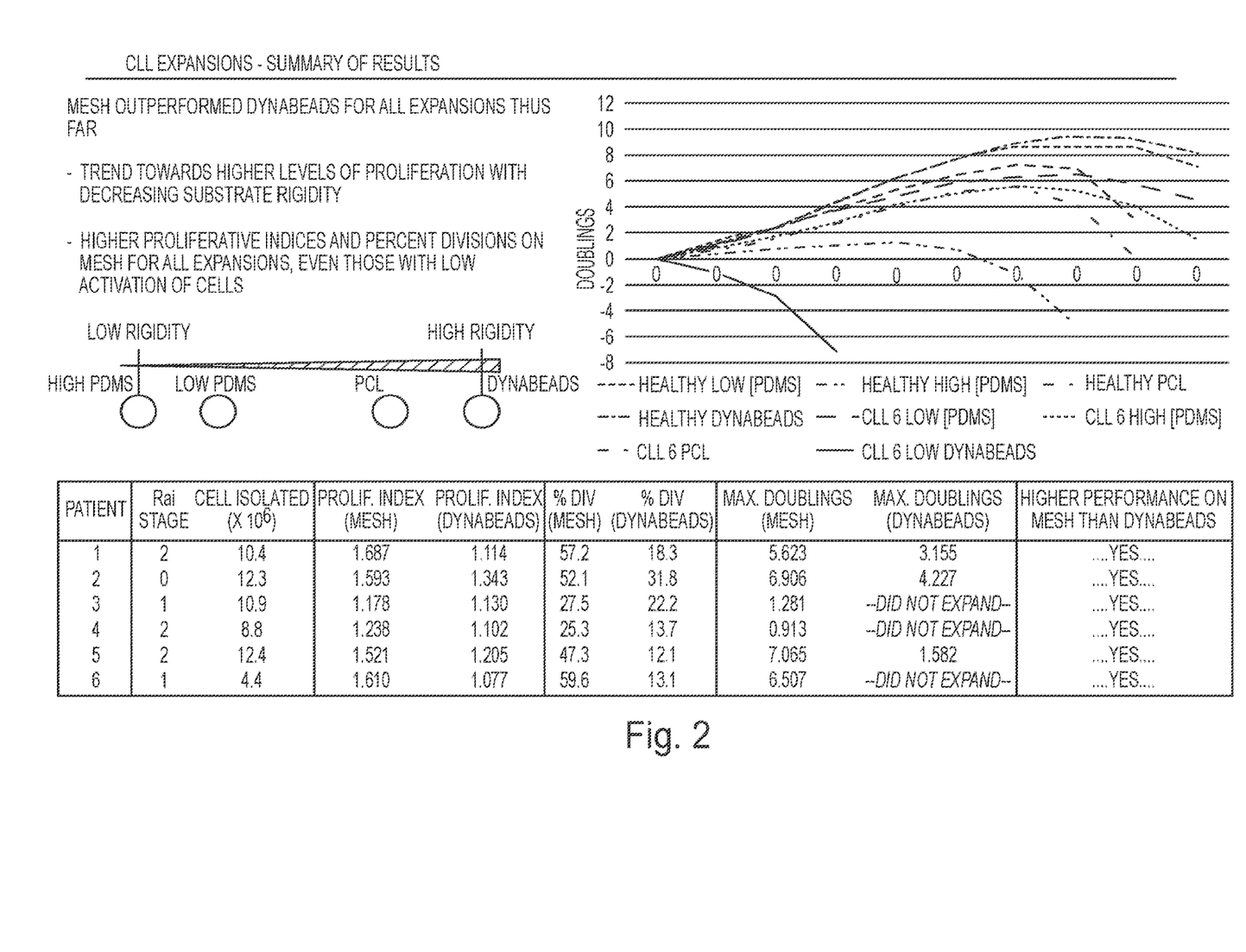
FIG. 2 shows a summary of the results of expansion comparing reference relative to embodiments described herein of the disclosed subject matter.
Figure 3A:
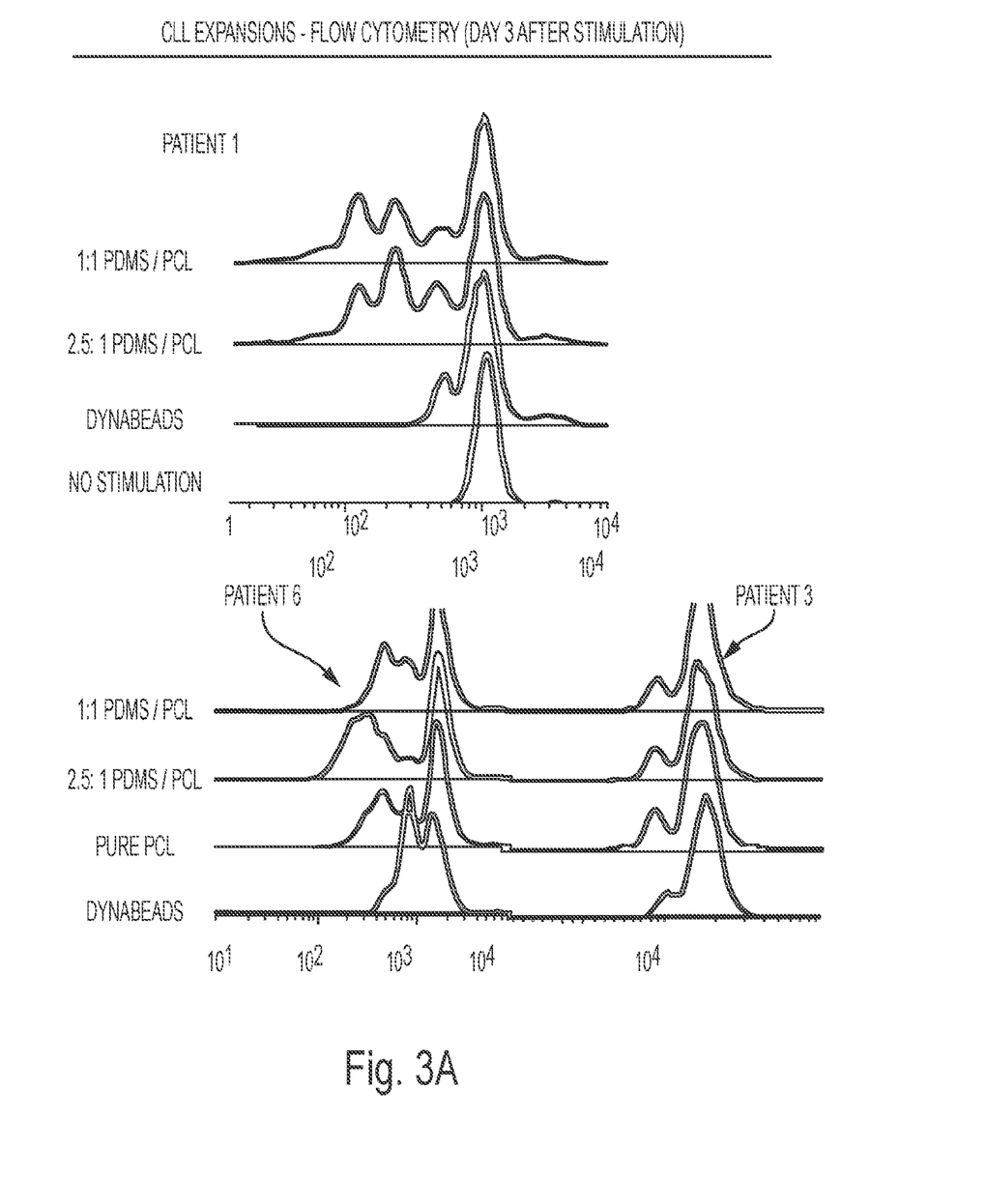
FIGS. 3A and 3B show results of flow cytometry comparing reference and present embodiments of the disclosed subject matter.
Figure 3B:
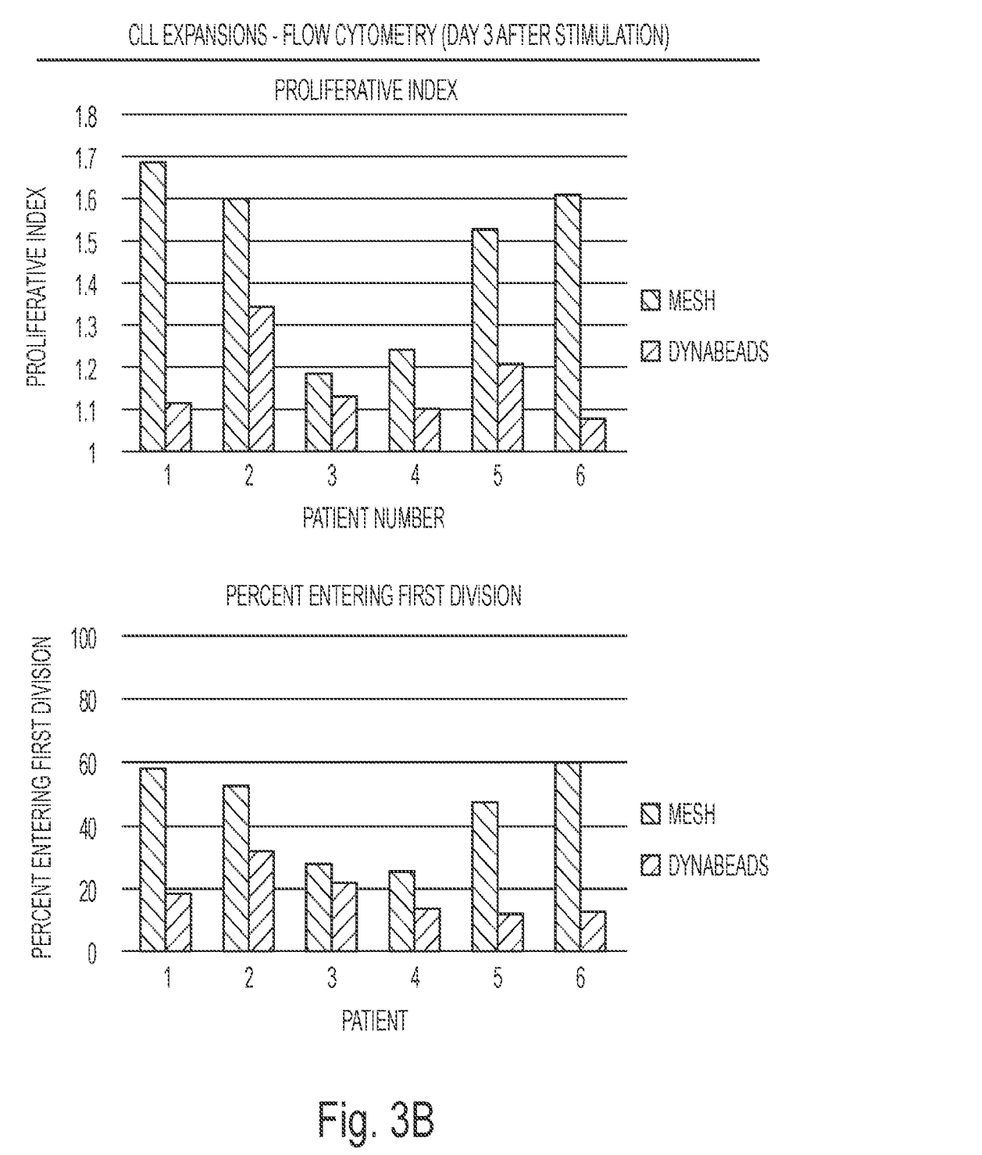
Figure 4A:
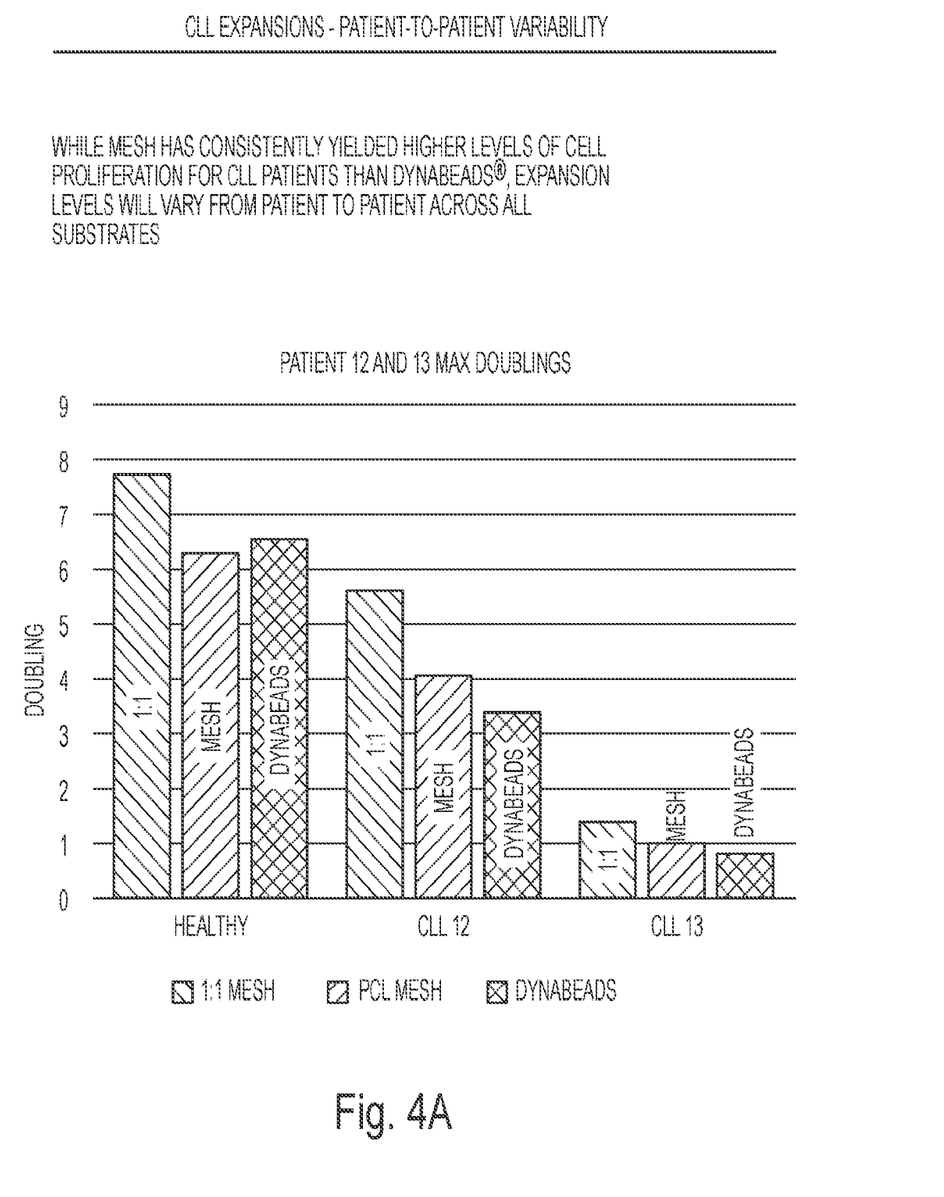
FIGS. 4A and 4B show expansion data comparing reference and current embodiments in terms of patient to patient variation according to embodiments of the disclosed subject matter.
Figure 4B:
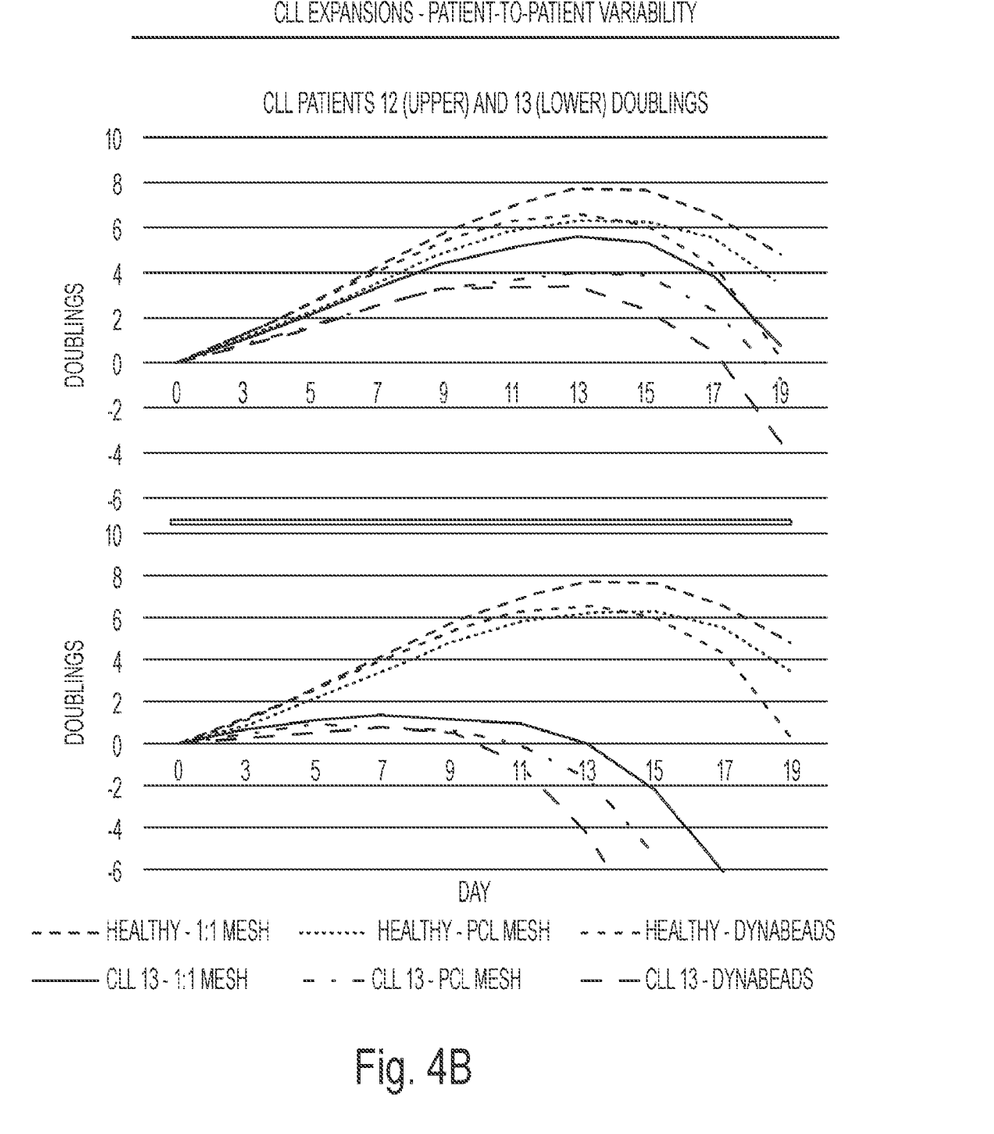
Figure 5:
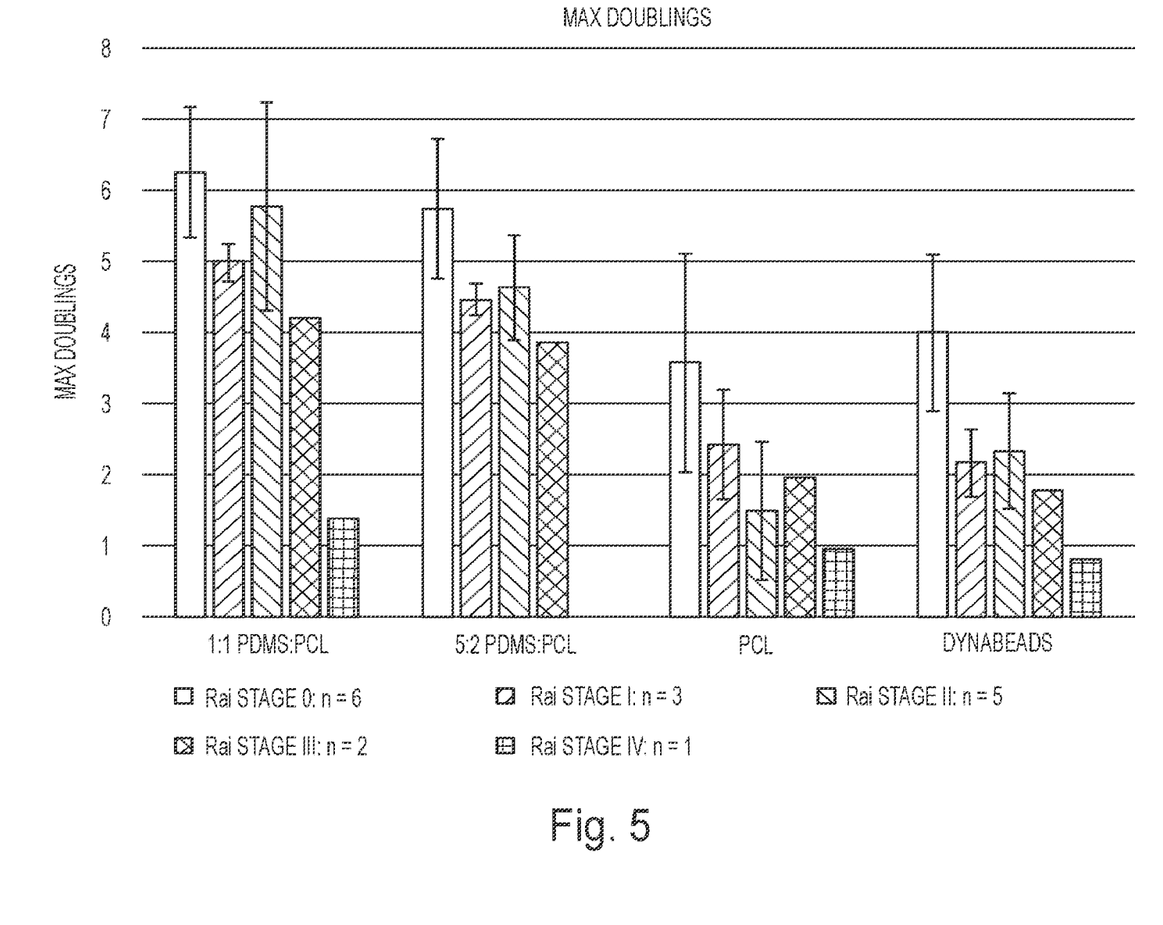
FIG. 5 shows expansion of cells from patients undergoing treatment for CLL-Max doublings as function of substrate and Rai according to embodiments of the disclosed subject matter.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DESCRIPTION

This disclosed subject matter includes a polymeric, microfibrous mesh designed primarily for, but not limited to, the ex vivo activation and proliferation (expansion) of human T cells for immunotherapeutic purposes. In an aspect, the primary non-biological components of this mesh comprise, consist of, or consist essentially of poly(dimethyl siloxane) (PDMS) and poly(caprolactone) (PCL). In an aspect, compositions, methods, and devices described herein provide a safer alternative to a current clinical standard for the ex vivo expansion of T cells that eradicates the possibility of residual amounts of activating substrate entering the patient while providing high levels of cell expansion and activation. In an aspect, the PDMS used herein is a medical grade PDMS.

T cells mechanosensing: As shown in the figures provided herein (T Cell Mechanosensing), T cells undergo mechanosensing. Higher levels of human T cell stimulation and proliferation are associated with decreasing substrate rigidity. Substrates are electrospun meshes and T cells obtained from healthy human donors. (see, for example, O'Connor et al. Journal of Immunology (2012)). The rigidity of the substrates (for example, $10^4$-$10^5$ Pa) described herein have a key role in leveraging T cell mechano-sensing ability. Laboratory results have demonstrated that softer materials promote greater cell expansion.

In an aspect, substrates described herein exhibit a rigidity of from about $10^3$ to about $10^6$ Pa, from about $10^4$ to about $10^6$ Pa, from about $10^5$ to about $10^6$ Pa, about $10^3$ to about $10^5$ Pa, or from about $10^4$ to about $10^5$ Pa.

In an aspect, the disclosure provides for a method of improving cell expansion comprising culturing cells on a mesh substrate described herein. In another aspect, the cells are T cells and/or stem cells.

In an aspect, the mesh substrate comprises and/or is spun from one or more of a synthetic polymer or copolymer prepared from at least one of the group of monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, .e-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-aminostyrene, p-amino-benzyl-styrene, sodium styrene sulfonate, sodium 2-sulfoxyethyl methacrylate, vinyl pyridine, aminoethyl methacrylates, 2-methacryloyloxytrimethylammonium chloride, N,N'-methylenebisacrylamide-, ethylene glycol dimethacrylates, 2,2'-(p-phenylene-dioxy)-diethyl dimethacrylate, divinylbenzene, triallylamine, and methylenebis-(4-phenyl-isocyanate).

In another aspect, the disclosure provides for a mesh substrate comprising, consisting of, or consisting essentially of polydimethylsiloxane and polycaprolactone. In another aspect, the mesh substrate or composition is described in, for example, U.S. Patent Application Publication No. 2017/0029767, the contents of which are hereby incorporated by reference in their entirety.

The disclosure also provides for a mesh substrate including fibers with a diameter of about 10 nm to about 1000 nm and a pore size of about 0.5 μm to about 100 μm. In another aspect, the disclosure provides for a mesh substrate including fibers with a diameter of about 0.5 μm to about 2 μm, about 10 nm to about 2000 nm or a diameter of about 10 nm to about 5000 nm. The disclosure further provides for a mesh substrate including fibers with a diameter of up to about 1000 nm, about 2000 nm, about 3000 nm, or about 5000 nm.

Further, the disclosure also provides for a mesh substrate including fibers with a diameter selected from about 25 nm to about 1000 nm, about 50 nm to about 750 nm, about 100 nm to about 500 nm, about 500 to about 800 nm, about 250 to about 1000 nm, about 1000 to about 2500 nm, about 200 nm to about 5000 nm, 100 nm to 20 μm, 300 nm to about 10 μm.

In another aspect, the disclosure provides for a mesh substrate comprising fibers with a pore size selected from the group consisting of about 1 μm to about 100 μm, about 1 μm to about 50 μm, about 1 μm to about 10 μm, and about 1 μm to about 5 μm.

The disclosure also provides for a substrate comprising polydimethylsiloxane and polycaprolactone in a ratio (w/w) selected from the group consisting of about 5:1, about 3:1, about 2.5:1, about 2:1, about 1:1, about 1:2, about 1:2.5, and about 1:5. In another aspect, the ratio of components can be modified in order to modify rigidity.

In an aspect, the cell expansion, for example stem cell or T-cell expansion, on a mesh substrate comprising polydimethylsiloxane and polycaprolactone is improved relative to polycaprolactone alone. In another aspect, cell expansion on a mesh substrate comprising polydimethylsiloxane and polycaprolactone is improved relative to polycaprolactone alone by at least about 10%, 20%, 30%, 40%, 50%, 60%, and 75%.

In an aspect, cell expansion, for example T-cell or Stem cell on a mesh substrate comprising polydimethylsiloxane and polycaprolactone is improved by about 10%, about 20%, about 30%, about 40%, about 50%, about 60%, or about 75% relative to polycaprolactone alone. In another aspect, cell expansion, for example T-cell or Stem cell on a mesh substrate comprising polydimethylsiloxane and polycaprolactone is improved by at least about 10%, at least about 20%, at least about 30%, at least about 40%, at least about 50%, at least about 60%, or at least about 75% relative to polycaprolactone alone. In another aspect, cell expansion, for example T-cell or Stem cell on a mesh substrate comprising polydimethylsiloxane and polycaprolactone is improved by about 10% to about 75%, about 10% to about 30%, about 20% to about 50%, about 30% to about 50% relative to polycaprolactone alone.

In an aspect, the PDMS used herein is a medical grade version of PDMS. In another aspect, PDMS and other components described herein are of such a quality that they are sufficient for use in human patient or subject experiments and/or treatments. In an aspect, MED-4086 PDMS is used herein. In yet another non-limiting aspect, the PDMS used herein is a medical grade version of PDMS. In yet another non-limiting aspect, SYLGARD 184 ("PDMS-A-hard") (Dow Corning) and/or NuSil med formulation 4086 ("PDMS-B") are used herein.

Adoptive Immunotherapy: As shown in, for example, the Figures, (adoptive Immunotherapy), may include Ex vivo expansion of patient's own immune cells. Comparative substrates for T cell expansion include, for example, Dynabeads®. Concerns for using such, however, may include safety and expansion of exhausted cell populations.

Chronic Lymphocytic Leukemia (CLL): As shown in the drawings (Chronic Lymphocytic Leukemia), CLL may include chronic overproduction of B cells from the bone marrow. There are approximately 19,000 new cases of CLL per year, which represents 35% of all leukemia cases. Average lifetime risk of developing CLL is about 1 in 200. Adoptive immunotherapy experiments have been performed in CLL studies. (See, for example, DeSantis C, Lin C, et al. CA: A Cancer Journal for Clinicians. 2014:64(4) 252-271, the contents of which are hereby incorporated by reference in their entirety).

In an aspect, compositions, substrates, and mesh products described herein may be used treat or expand cells herein. In another aspect, compositions, substrates, and mesh products described herein may be used to treat or expand leukemia cells, for example, CLL.

Methodology: The drawings (Methodology) shows, for example, a process that may include culturing isolated human T cell (e.g., CD4/8) on mesh substrates, which are fabricated with functionalization, e.g., coating with antibodies, proliferating cells, and activating (or stimulating) cells.

Fabrication: As shown in the drawings (Electrospinning), the mesh is made via electrospinning from a mixture of PDMS (facile modulation of rigidity) and PCL (viscosity modulator) where the ratio of the first agent to the second agent is higher than or equal to 1. Electrospinning feeds are made by dissolving PDMS-PCL mixtures in a 3:1 v:v solution of dichloromethane (DCM) and N—N-dimethyl formamide (DMF). Meshes are fabricated such that fibers are approximately 1.0-1.2 μm in diameter and pores are approximately 10-11 μm in diameter.

Functionalization: Following electrospinning, as shown in the drawings (Substrate Functionalization), meshes are coated with a layer of antibodies prior to cell stimulation. A primary capture antibody layer of goat-anti-mouse IgG is bonded via direct adsorption to the mesh followed by a secondary layer of activating antibodies. This second layer is composed of a 3:1 mol:mol ratio of mouse IgG-anti-human CD28 and mouse IgG-anti-human CD3.

Substrate Characterization: As shown in the drawings (Substrate Characterization—SEM/FTIR), FTIR indicates dispersal and proper ratio of PCL in PDMS and fiber diameters from ~1-2 μm, pore diameters as function of polymer wt. %.

Usage: In an aspect, compositions described herein are designed for the ex vivo expansion of human T cells from healthy patients, patients suffering from long-term chronic illnesses, and healthy patients and patients suffering from long-term chronic illnesses. In this usage, isolated cells are stimulated on the mesh for about, for example, 1 day, about 2 days, about 3 days, about 4 days, about 5 days or more followed by continued culture without mesh stimulation. In an aspect, expanded cells are removed from culture upon completion of the initial blast phase.

In an aspect, the disclosure provides for expansion of T cells from healthy patients as well with patients suffering from chronic lymphocytic leukemia (CLL) using methods described herein.

In an aspect, long-term expansion is achieved for 19 days, separation based on RAI stage. In another aspect, long-term expansion is achieved for about 10 to about 20 days, about 15 to about 25 days, or about 5 to about 30 days separation based on RAI stage.

In another aspect, the disclosure provides for fewer doublings with increasing RAI stage across all substrate types.

The disclosure and Figures further provide for (a) secondary stimulation after finishing blast phase (V<400 fL), t=4 h, (b) CD107b (LAMP-2): expressed on inner surface of exocytosed granzyme-containing vesicles, typical for CD8+ cells, (c) IFNγ (Interferon gamma): soluble cytokine, biomarker for cytotoxic activity, and (d) Mesh-expanded cells as functional as Dynabead®-expanded cells.

In an aspect, the description and Figures exhibit higher levels of doublings observed with MED 4086 mesh than planar slab. The drawings (Supplemental Data II-Mesh Alignment and Fiber Diameter) shows upper limit to fiber formation.

The drawings (Supplemental Data III-$V_H$ Mutation Levels) shows (a) 2002 review paper by Stilgenbauer et al in Leukemia, (b) Study of 300 adults 18-64 y/o over 14 years, (c) VII mutation levels: <2% mutated=higher risk of CLL progression, 2-20% mutated=lower risk of CLL progression, Un-mutated VH group died out almost twice as quickly as mutated $V_H$ group.

The mesh, substrates, compositions, and methods described herein display, for example, (1) higher levels of T cell proliferation on PDMS/PCL meshes than on Dynabeads®, (2) Comparable levels of cellular activity between PDMS/PCL meshes and Dynabeads®, (3) Decreasing levels of maximal cell proliferation with increasing RAI stage.

EXAMPLES

Example 1—PDMS/PCL Electrospinning (Lu Lab Fume Hood, Engineering Terrace 364)

Example 1 provides for a representative process of preparing a composition and substrate described herein.
Preparing the spinning feed (Engineering Terrace 399 A)
1) In an aspect, PDMS, along with small aliquots of DCM (dichloromethane) and DMF (dimethyl formamide) are used. For MED-4086, a 1:1 ratio of part A to part B is mixed and vortexed for 5 minutes. To degas, spin at 300 rpm for another 3 minutes, or rather, until the bubbles are all gone.
2) For PCL, a viscosity modulator may be added (PDMS has too low of a molecular weight), and the amount of PCL to add depends on whether or not micro or nano fibers are desired. In an aspect, the disclosure provides for a ratio of DCM:DMF, which is added in a 4:1 ratio (v:v).

TABLE 1

| Pure PCL | — | 480 mg PCL | 0.75 mL DMF | 2.25 mL DCM |
|---|---|---|---|---|
| 1:1 (nano) | 800 mg PDMS | 800 mg PCL | 2.11 mL DMF | 6.33 mL DCM |
| 1:1 (micro) | 800 mg PDMS | 800 mg PCL | 1.14 mL DMF | 3.43 mL DCM |
| 2.5:1 | 1.14 g PDMS | 457 mg PCL | 0.89 mL DMF | 2.67 mL DCM |
| 3:1 | 1.20 g PDMS | 400 mg PCL | 0.80 mL DMF | 2.40 mL DCM |
| 4:1 | 1.24 g PDMS | 320 mg PCL | 0.67 mL DMF | 2.00 mL DCM |

3) In another aspect, the vials are taped securely to a vortex, and vortex on medium speed for 3-5 hours. For an overnight mixing, a shaker, for example an orbital shaker, may be used. In an aspect, the vial may be optionally vortexed for about 1 hour.

Electrospinning
4) In an aspect, a 5 mL syringe with a 25 G needle, working distance=10-12 cm., voltage=10-11 kV, is spun, for example, at 1 mL/h. If aligned fibers are desired, the sample may be spun at about 2000-2400 RPM. For example, in an aspect, an 8 hour spin provides a ~100 μm thick mesh with the 2.5:1 formulation The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features. It is, thus, apparent that there is provided, in accordance with the present disclosure, methods and systems for cell expansion. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:
1. A method of improving cell expansion comprising:
(a) culturing cells for at least 3 days on a mesh substrate comprising polydimethylsiloxane and polycaprolactone, wherein the cells are T lymphocytes of a patient suffering from chronic lymphocytic leukemia (CLL),
(b) wherein said mesh comprises electrospun fibers with rigidity of $10^3$ to $10^6$ Pa, wherein the fibers are coated with antibodies comprising anti-CD3 antibody and anti-CD28 antibody, and
(c) wherein the fibers have diameters of 0.5 to 5 micron.
2. The method of claim 1, wherein said cells are
i. isolated from an individual,
ii. expanded in vitro, and
iii. transfused back to an individual in need thereof.
3. The method of claim 1, wherein the CLL is at Rai stage 0, 1, 2, 3, 4, or 5.

4. The method of claim 1, wherein the CLL is at Rai stage 2.

5. The method of claim 1, wherein said mesh substrate consists essentially of polydimethylsiloxane and polycaprolactone.

\* \* \* \* \*